(12) United States Patent
Williams

(10) Patent No.: US 8,666,511 B2
(45) Date of Patent: Mar. 4, 2014

(54) MAGNETIC RESONANCE IMAGING COMPATIBLE MEDICAL ELECTRICAL LEAD AND METHOD OF MAKING THE SAME

(75) Inventor: Terrell M. Williams, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/561,564

(22) Filed: Jul. 30, 2012

(65) Prior Publication Data

US 2014/0031911 A1    Jan. 30, 2014

(51) Int. Cl.
*A61N 1/05*    (2006.01)

(52) U.S. Cl.
USPC ........................................................ 607/119

(58) Field of Classification Search
USPC ........................................................ 607/119
See application file for complete search history.

(56) References Cited

U.S. PATENT DOCUMENTS

| | | | |
|---|---|---|---|
| 4,840,186 A | 6/1989 | Lekholm et al. | |
| 5,201,903 A | 4/1993 | Corbett, III et al. | |
| 5,466,253 A | 11/1995 | Doan | |
| 5,845,396 A | 12/1998 | Altman et al. | |
| 6,249,708 B1 | 6/2001 | Nelson et al. | |
| 7,783,365 B2 | 8/2010 | Ebert et al. | |
| 7,844,343 B2 | 11/2010 | Wahlstrand et al. | |
| 8,209,032 B2 | 6/2012 | Ebert et al. | |
| 2006/0229693 A1 | 10/2006 | Bauer et al. | |
| 2006/0293737 A1 | 12/2006 | Krishnan | |
| 2007/0179577 A1 | 8/2007 | Marshall et al. | |
| 2007/0179582 A1 | 8/2007 | Marshall et al. | |
| 2007/0185556 A1 | 8/2007 | Williams et al. | |
| 2007/0208383 A1 | 9/2007 | Williams | |
| 2007/0239249 A1 | 10/2007 | Tockman | |
| 2008/0132985 A1 | 6/2008 | Wedan et al. | |
| 2009/0149920 A1 | 6/2009 | Li et al. | |
| 2009/0157156 A1 | 6/2009 | Foster | |
| 2009/0192577 A1 | 7/2009 | Desai | |
| 2009/0198314 A1 | 8/2009 | Foster et al. | |
| 2010/0049290 A1 | 2/2010 | Min et al. | |
| 2010/0160989 A1 | 6/2010 | Legay | |
| 2010/0204766 A1* | 8/2010 | Zdeblick et al. | 607/119 |
| 2011/0034983 A1 | 2/2011 | Min et al. | |
| 2011/0137369 A1 | 6/2011 | Ryu et al. | |
| 2011/0160817 A1 | 6/2011 | Foster et al. | |
| 2011/0270369 A1 | 11/2011 | Tekmen et al. | |
| 2012/0043011 A1 | 2/2012 | Claude et al. | |
| 2012/0136422 A1 | 5/2012 | Ebert et al. | |
| 2012/0188042 A1 | 7/2012 | Claude et al. | |

FOREIGN PATENT DOCUMENTS

WO    2012038378 A1    3/2012

* cited by examiner

*Primary Examiner* — George Manuel
(74) *Attorney, Agent, or Firm* — Michael J. Ostrom

(57) ABSTRACT

This disclosure describes an implantable medical lead, and method of making such a lead, that reduces the undesirable effects the fields generated by an MRI device may have on the implantable medical lead and the implantable medical device. The implantable medical lead has a proximal end configured to connect to an implantable medical device and a distal end. The lead also includes at least one electrode located near the distal end and at least one coiled conductor that extends along a length of the lead from the proximal end to a respective electrode. The lead further includes an outer jacket that is configured to only partially extend between turns of one or more of the coiled conductors.

26 Claims, 13 Drawing Sheets

MAGNETIC RESONANCE IMAGING COMPATIBLE MEDICAL ELECTRICAL LEAD AND METHOD OF MAKING THE SAME

TECHNICAL FIELD

The present disclosure relates to implantable medical leads and methods of manufacturing such leads.

BACKGROUND

Implantable leads are used in conjunction with a wide variety of medical devices to form medical systems for delivering therapy to a patient or sensing physiological parameters of the patient. For example, implantable leads are commonly connected to implantable pacemakers, defibrillators, cardioverters, or the like, to form an implantable cardiac system that provides electrical stimulation to the heart or sensing of electrical activity of the heart. The electrical stimulation pulses can be delivered to the heart and the sensed electrical signals can be sensed by electrodes disposed on the leads, e.g., typically near distal ends of the leads. In that case, the leads may be implanted such that the electrodes are positioned with respect to various cardiac locations so that the cardiac device can deliver pulses to or sense activity of the appropriate locations. Implantable leads are also used for stimulation of other tissue, muscle, or nerve, such as in neurological devices, muscular stimulation therapy, gastric system stimulators and other implantable medical devices (IMDs).

Occasionally, patients that have implantable leads may benefit, or even require, various medical imaging procedures to obtain images of internal structures of the patient. One common medical imaging procedure is magnetic resonance imaging (MRI). MRI procedures may generate higher resolution and/or better contrast images (particularly of soft tissues) than other medical imaging techniques. MRI procedures also generate these images without delivering ionizing radiation to the body of the patient, and, as a result, MRI procedures may be repeated without exposing the patient to such radiation.

During an MRI procedure, the patient or a particular part of the patient's body is positioned within an MRI device. The MRI device generates a variety of magnetic and electromagnetic fields to obtain the images of the patient, including a static magnetic field, gradient magnetic fields, and radio frequency (RF) fields. The static MRI field may be generated by a primary magnet within the MRI device and may be present prior to initiation of the MRI procedure. The gradient magnetic fields may be generated by electromagnets of the MRI device and may be present during the MRI procedure. The RF magnetic field may be generated by transmitting/receiving coils of the MRI device and may be present during the MRI procedure. If the patient undergoing the MRI procedure has an implantable medical system, the various fields produced by the MRI device may have undesirable effects on the medical leads or the medical device to which the leads are coupled. For example, the gradient magnetic fields or the RF fields generated during the MRI procedure may induce energy on the implantable leads (e.g., in the form of a current), which may be conducted to tissue proximate to the electrode and cause a rise in temperature of the tissue.

SUMMARY

This disclosure describes an implantable medical lead, and method of making such a lead or components of the lead, that reduces the undesirable effects the fields generated by an MRI device may have on the implantable medical lead and the implantable medical device. In one example, this disclosure is directed to an implantable medical lead having a proximal end configured to connect to an implantable medical device and a distal end. The lead includes a plurality of electrodes located near a distal end of the lead and a plurality of coiled conductors, each of which extend along a length of the lead from the proximal end to a respective one of the plurality of electrodes located near the distal end. The lead also includes an outer jacket that is configured to only partially extend between turns of at least one of the plurality of coiled conductors.

In another example, this disclosure is directed to an implantable medical lead having a proximal end configured to connect to an implantable medical device and a distal end. The lead comprises at least one electrode located near a distal end of the lead. The lead also includes at least one coiled conductor extending along a length of the lead from the proximal end to the electrode located near the distal end and which is electrically coupled to the electrode. The lead includes an outer jacket that is configured to only partially extend between turns of the coiled conductor.

In a further example, this disclosure provides a method comprising obtaining a mandrel having a first end and a second end, winding one or more conductors around the mandrel from the first end of the mandrel to the second end of the mandrel, placing a substrate material of a lead outer jacket over the wound conductors, and reflowing the substrate material such that the lead outer jacket extends only partially between turns of the wound conductors.

Although described mainly in the context of MRI procedures, the implantable medical leads of this disclosure may also allow the patient to undergo other medical procedures that utilize high frequency signals that may affect operation of the medical electrical lead, such as electrocautery procedures, diathermy procedures, ablation procedures, electrical therapy procedures, magnetic therapy procedures, or the like. Moreover, the implantable medical leads described in this disclosure may also reduce the effects of high frequency signals encountered in medical and non-medical environments, such as in an environment with radio frequency identification (RFID) reading devices including surgeries that utilize RFID tagged instruments, towels, or the like.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
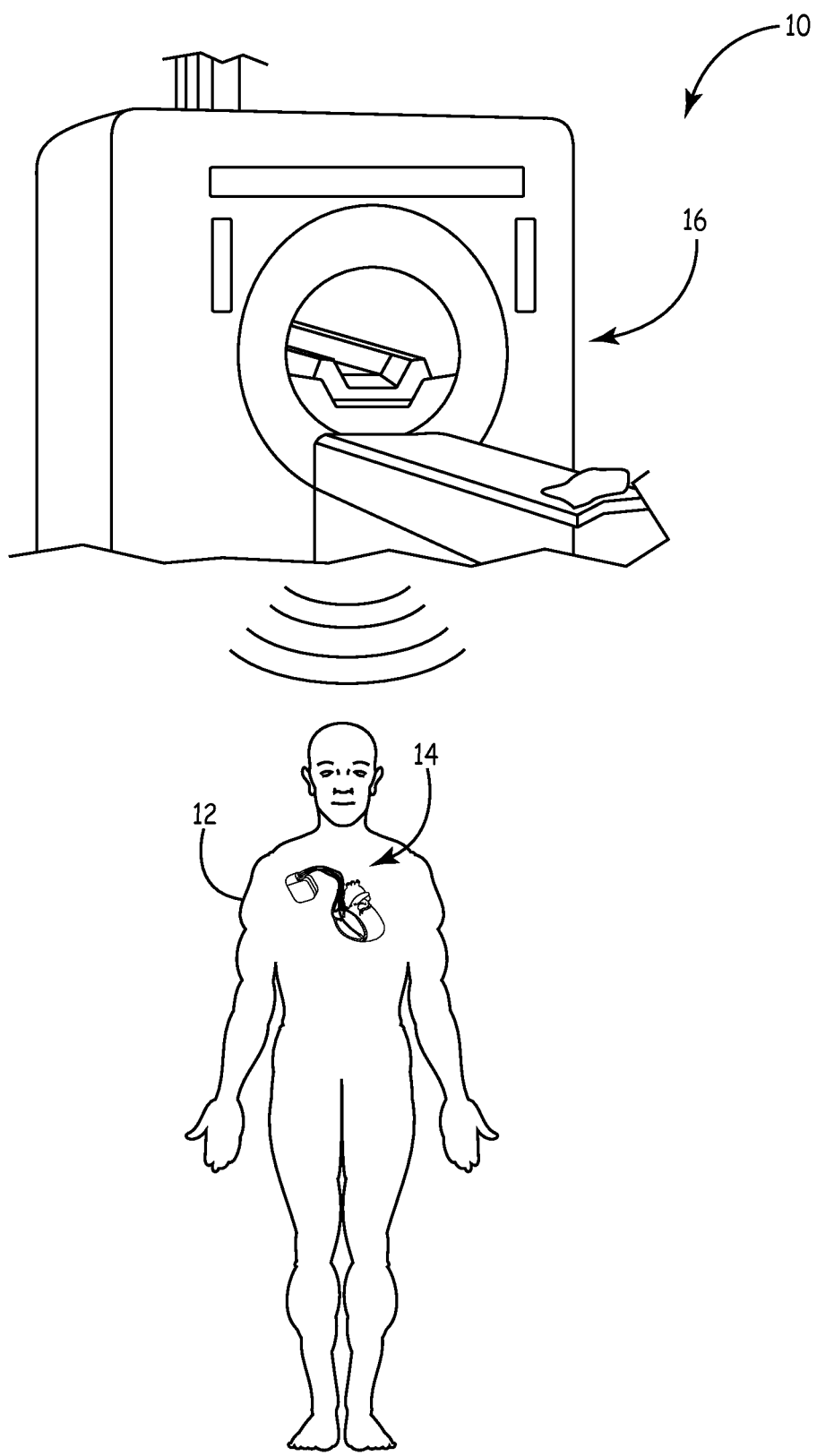
FIG. 1 is a conceptual diagram illustrating a magnetic resonance imaging (MRI) environment that includes an MRI device.

FIG. 1 is a conceptual diagram illustrating a magnetic resonance imaging (MRI) environment 10 that includes an MRI device 16. MRI device 16 may include a patient table on which patient 12 is placed prior to and during an MRI scan. The patient table is adjusted to position at least a portion of patient 12 within a bore of MRI device 16 (the "MRI bore"). While positioned within the MRI bore, the portion of patient 12 being scanned is subjected to a number of magnetic and RF fields to produce images of body structures for diagnosing injuries, diseases, and/or disorders.

MRI device 16 includes a scanning portion that houses a primary magnet of MRI device 16 that generates a static MRI field. The static MRI field is a large non time-varying magnetic field that is typically always present around MRI device 16 whether or not an MRI procedure is in progress. MRI device 16 also includes a plurality of gradient magnetic field coils that generate gradient magnetic fields. Gradient magnetic fields are pulsed magnetic fields that are typically only present while the MRI procedure is in progress. MRI device further includes one or more RF coils that generate RF fields. RF fields are pulsed high frequency fields that are also typically only present while the MRI procedure is in progress. Although the structure of MRI devices may vary, it is contemplated that the techniques used herein to detect the static MRI field, which is generally applicable to a variety of other MRI device configurations, such as open-sided MRI devices or other configurations.

The magnitude, frequency or other characteristic of the static MRI field, gradient magnetic fields and RF fields may vary based on the type of MRI device 16 producing the field or the type of MRI procedure being performed. A 1.5 T MRI device, for example, will produce a static magnetic field of approximately 1.5 Tesla and have a corresponding RF frequency of approximately 64 megahertz (MHz) while a 3.0 T MRI device will produce a static magnetic field of approximately 3.0 Tesla and have a corresponding RF frequency of approximately 128 MHz. However, other MRI devices may generate different fields that may be detected in accordance with the techniques of this disclosure.

Figure 2:
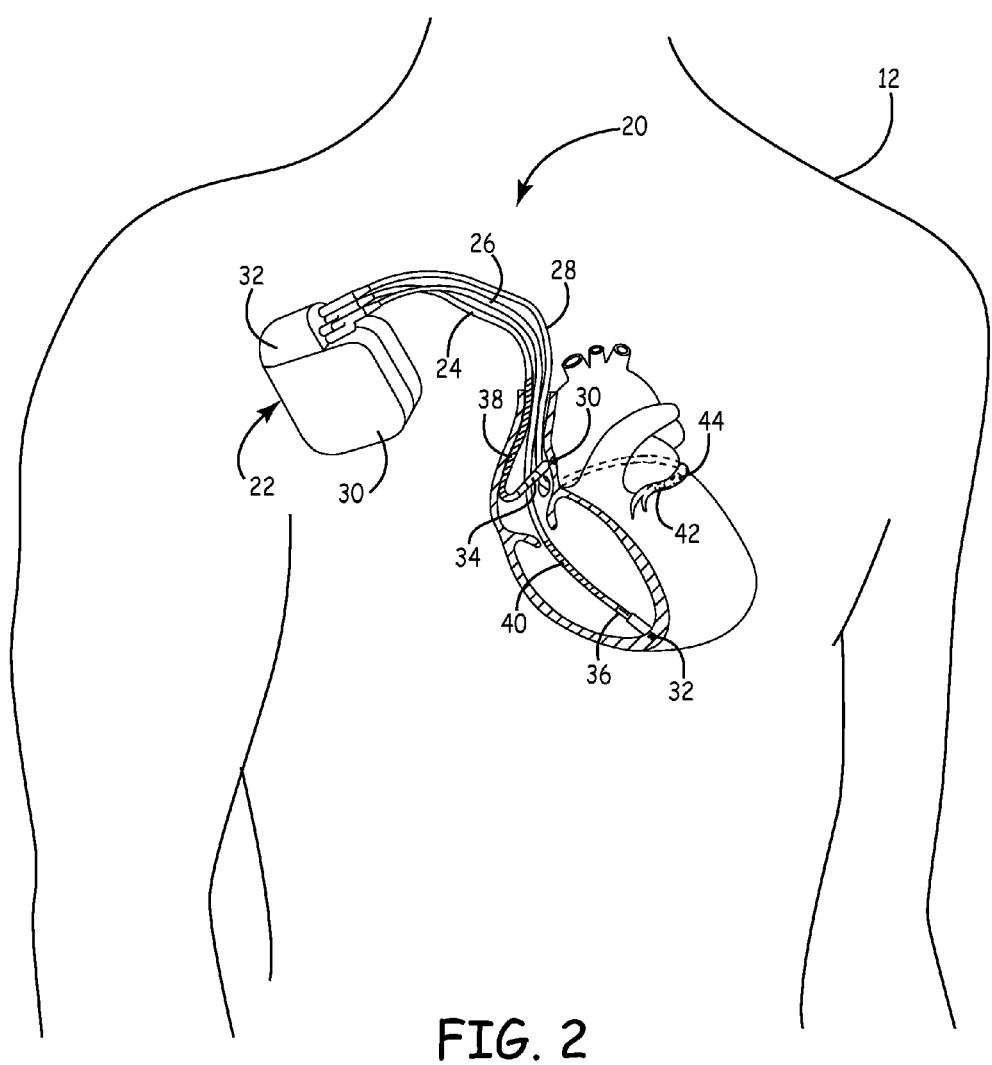
FIG. 2 is a conceptual diagram illustrating an example implantable medical system.

Patient 12 is implanted with an implantable medical system 14. In one example, implantable medical system 14 may include an IMD connected to one or more leads, as illustrated in FIG. 2 in more detail. The IMD may be an implantable cardiac device that senses electrical activity of a heart of patient 12 and/or provides electrical stimulation therapy to the heart of patient 12. For example, the IMD may be an implantable pacemaker, implantable cardioverter defibrillator (ICD), cardiac resynchronization therapy defibrillator (CRT-D), cardioverter device, or combinations thereof. Although implantable medical system 14 is described throughout this disclosure as an implantable cardiac system (e.g., a pacemaker system, ICD system, CRT-D system, or the like), in other examples, an implantable medical system may include an implantable medical system that provides stimulation to other muscles, nerves, or tissue, such as a deep brain stimulation system, vagus nerve stimulation system, gastric stimulation system, pelvic floor stimulation system, spinal cord stimulation system, or other stimulation system.

Some or all of the various types of fields produced by MRI device 16 may have undesirable effects on implantable medical system 14. In one example, the gradient magnetic fields and/or the RF fields generated during the MRI procedure may induce energy on the conductors of the leads (e.g., in the form of a current). The induced energy on the leads may be conducted to tissue proximate to an electrode of the leads and cause a rise in temperature of the tissue. One or more medical leads of the implantable medical system are designed to reduce the undesirable effects the fields produced by MRI device 16 may have on the leads. For example, the implantable medical lead may be designed and constructed in accordance with the techniques of this disclosure such that much of the energy induced on the conductors of the lead are dissipated to the body along a substantial portion of the length of the lead.

Although described mainly in the context of MRI procedures, leads constructed in accordance with the techniques of this disclosure may also allow the patient to undergo other medical procedures that generate external fields (such as high frequency RF signals) that may affect operation of the medical electrical lead, such as electrocautery procedures, diathermy procedures, ablation procedures, electrical therapy procedures, magnetic therapy procedures, or the like. Moreover, the medical electrical leads described in this disclosure may also reduce the effects of high frequency signals encountered in medical and non-medical environments, such in an environment with RFID reading devices including surgeries that utilize RFID tagged instruments, RF security gates, or the like.

FIG. 2 is a conceptual diagram illustrating an example implantable medical system 20, which may correspond with implantable medical system 14 of FIG. 1. Medical system 20 includes IMD 22 connected to leads 24, 26, and 28. IMD 14 may be an implantable cardiac device that senses electrical activity of a heart of patient 12 and/or provides electrical stimulation therapy to the heart of patient 12. IMD 14 may, for example, be an implantable pacemaker, implantable cardioverter defibrillator (ICD), cardiac resynchronization therapy defibrillator (CRT-D), cardioverter device, or combinations thereof. IMD 14 may alternatively be a non-cardiac implantable device, such as an implantable neurostimulator or other device that provides electrical stimulation therapy to other muscles, tissues, or nerves of the patient.

IMD 22 includes a housing 30 within which components of IMD 22 are housed. Housing 30 can be formed from conductive materials, non-conductive materials or a combination thereof. IMD 22 includes a power source, such as a rechargeable or non-rechargeable battery, that provides power to one or more electrical components of IMD 22. The electrical components may include one or more processors, memories, transmitters, receivers, sensors, sensing circuitry, therapy circuitry and other appropriation components.

The example implantable medical system 20 illustrated in FIG. 2 includes leads 24, 26, and 28 coupled to IMD 22 via connector block 32 (sometimes referred to as a header). In some examples, proximal ends of leads 24, 26 and 28 may include electrical contacts that electrically couple to respective electrical contacts within connector block 32 and, ultimately, are electrically coupled to electrical components (e.g., sensing circuitry or therapy circuitry) of IMD 22. In addition, in some examples, leads 24, 26 and 28 may be mechanically coupled to connector block 32 with the aid of set screws, connection pins or another suitable mechanical coupling mechanism.

Leads 24, 26 and 28 extend from IMD 22 into the heart of patient 12. In the example shown in FIG. 2, lead 24 extends from IMD 22 into the right atrium of the heart of patient 12, lead 26 extends from IMD 22 into the right ventricle of the heart of patient 12, and lead 28 extends into the coronary sinus to a region adjacent to the left ventricle of the heart of patient 12. Leads 24, 26 and 28 include respective electrodes located near or at a distal end of leads 24, 26 and 28. Leads 24 and 26 include respective tip electrodes 30 and 32 and ring electrodes 34 and 36. Tip electrodes 30 and 32 are illustrated in FIG. 2 as extendable helix tip electrodes mounted retractably within the distal end of lead 24 and 26, respectively. In the case of a helix tip electrode, a portion of tip electrodes 30 and 32 also function as the fixation mechanism via with the distal end of leads 24 and 26 are affixed within the heart of patient 12. Tip electrodes 30 and 32 may be shaped into fixation mechanisms having shapes other than the helical shapes illustrated in FIG. 2. In other instances, tip electrodes 30 and 32 of one or both of leads 24 and 26 may take other forms, such as a generally spherical, hemispherical, or ring-shaped electrode that do not readily lend themselves to function as the fixation mechanism. In this case, leads 24 or 26 may include passive fixation mechanisms, such as tines, hooks, grapple mechanisms, or any other fixation mechanism that does not function as part of the tip electrode.

Leads 24 and 26 also include respective defibrillation electrodes 38 and 40 for delivery of high voltage defibrillation and/or cardioversion therapy to the heart of patient 12. Defibrillation electrodes 38 and 40 may be elongated electrodes which may, in some instances, take the form of a coil. In other embodiments, however, leads 24 and 26 include more or fewer electrodes than illustrated in FIG. 2. For instance, one or both of leads 24 and 26 may include multiple defibrillation electrodes. For example, lead 26 may include an RV defibrillation electrode and an SVT defibrillation electrode. In this example, lead 24 may not have a defibrillation electrode. In another example, neither of leads 24 or 26 may include a defibrillation electrode. Leads 24 and 26 may also include additional ring electrodes.

Lead 28 includes a plurality of electrodes located near the distal end of lead 28. In the example illustrated in FIG. 2, lead 28 is a multi-polar lead that includes two electrodes 42 and 44 located near the distal end of the lead. Electrodes 42 and 44 may be ring electrodes. However, in other examples, lead 28 may include a tip electrode, such as a spherical or hemispherical tip electrode instead of ring electrode 42. However, lead 28 may include more or fewer electrodes. For example, lead 28 may be a multipolar lead that includes three, four, or more electrodes. Lead 28 includes a passive fixation mechanism (not shown) that does not function as part of one of electrodes.

Leads 24, 26, and 28 include a plurality of conductors (not shown in FIG. 2) that extend along a length of leads 24, 26, and 28 from connector block 27 to engage with respective electrodes 30, 32, 34, 36, 38, 40, 42 and 44. In this manner, each of the electrodes 30, 32, 34, 36, 38, 40, 42 and 44 is electrically coupled to a respective conductor within its associated lead bodies. In other instances, more than one conductor may be coupled to at least some of electrodes 30, 32, 34, 36, 38, 40, 42 and 44 such that some of the electrodes are associated with more than one conductor. In still other instances at least one of the conductors may be electrically coupled to more than one electrode such that a single conductor may be associated with more than one electrode. The respective conductors may couple to circuitry, such as a therapy module or a sensing module, of IMD 22 via connections in connector block 32 and one or more feedthroughs (not shown). The electrical conductors transmit therapy from the therapy module within IMD 22 to one or more electrodes 30, 32, 34, 36, 38, 40, 42 and 44 and transmit sensed electrical signals from one or more electrodes 38, 40, 42 and 44 to the sensing module within IMD 22. The conductors within leads 24, 26, and 28 may be coiled conductors also have a conductive core and, in some instances, an insulation layer surrounding the conductive core.

An outer jacket of some or all of leads 24, 26, and 28 may be formed from a non-conductive, biocompatible material, including but not limited to silicone, polymers (e.g., polyurethane), fluoropolymers, thermoplastic, or mixtures thereof, or any other appropriate materials shaped to form a lumen within which the conductors extend. In other instances, the outer jacket of some or all of leads 24, 26, and 28 may formed from a conductive or semi-conductive, biocompatible material, including but not limited to conductive polymers. The outer jacket of some or all of leads 24, 26, and 28 may be constructed such that much of the current induced on the electrical conductors of the lead(s) from the various fields of MRI device 16 may be dissipated along the length of the lead without affecting the efficacy of low frequency current associated with electrical stimulation therapy (e.g., pacing, cardioversion, defibrillation, etc).

Figure 3A:
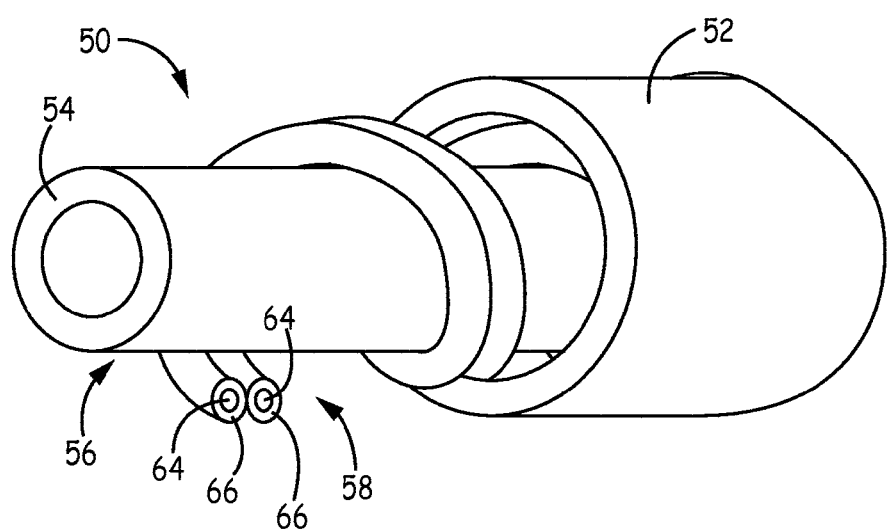
FIGS. 3A and 3B illustrate a partially cut away perspective view and a cross sectional view, respectively, along a length of a portion of an example lead.
Figure 3B:
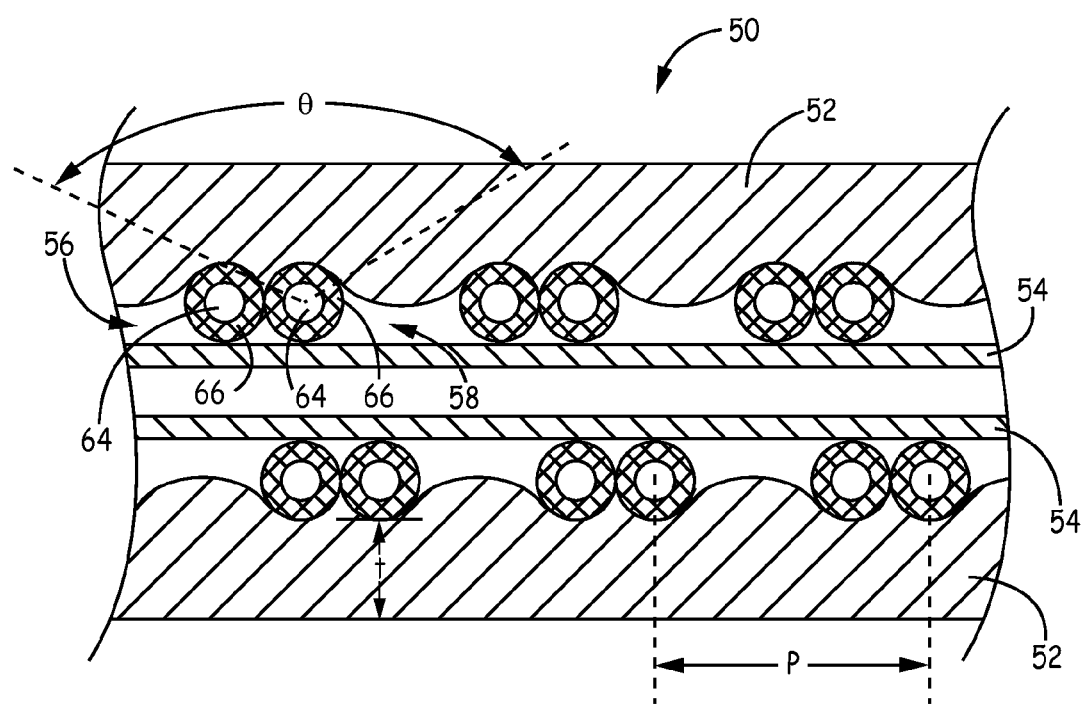

FIGS. 3A and 3B illustrate a portion of an example lead 50, which may correspond with one or more of leads 24, 26, or 28 of FIG. 2, in further detail. FIG. 3A illustrates a partially cut away perspective view of a portion of lead 50. FIG. 3B illustrates a cross sectional view along a length of a portion of lead 50. Lead 50 includes an outer jacket 52, an inner tubing 54, and conductors 56 and 58.

Conductors 56 and 58 extend along the length of the lead and electrically couple with respective electrodes near the distal end of lead 50, such as electrodes 42 and 44 illustrated in FIG. 2. In this manner, conductors 56 and 58 provide an electrical path from the proximal end of lead 50 configured to connect to IMD 22 to electrodes 42 and 44 located at the distal end of lead 50. As described above with respect to FIG. 2, conductors may conduct electrical stimulation from IMD 22 to electrodes 42 and 44 and/or conduct electrical signals from electrodes 42 and 44 to IMD 22.

Conductors 56 and 58 are each wound around inner tubing 54 such that they extend along a helical path from the proximal end of lead 50 to the distal end of lead 50 to form coiled conductors having a plurality of turns. As such, the conductors may be referred to herein as coiled conductors 56 and 58. Inner tubing 54 comprises a non-conductive or insulating material, such silicone, polyurethane, polyethylene, or other polymer, fluoropolymer, thermoplastic, or other non-conductive material, or combination of materials. In one example, inner tubing 54 may be made from a surface modified material, such as a surface modified polymer. The surface modified polymer may be modified to provide reduced friction of the inner tubing 54 (increased lubricity), which provides improved interaction with a stylet or guidewire. In another example, inner tubing 54 may include multiple layers of materials with an innermost layer being of a material that provides reduced friction, such as Teflon®.

The conductors of lead 50 are configured in a co-radial configuration in which conductors 56 and 58 are wound side by side to form coils having substantially the same radius. For example, the conductors 56 and 58 are wound around a single axis (e.g. the longitudinal axis of lead 50) and have substantially similar radius with respect to the single axis. Although the techniques of this disclosure are described in the context of co-radially wound conductors, the techniques may also be utilized with co-axial lead configurations. For example, the techniques described herein may be used in the context of a co-axial lead in which the coiled conductors have different radii to form inner and outer conductive coils. In this case, outer jacket 52 may only extend partially between the turns of the outer coiled conductor of the co-axial lead configuration (e.g., the coiled conductor having the largest radius). Moreover, the techniques of this disclosure may be further utilized with some or all of the conductors of leads having cable conductors or even in multi-lumen lead configurations.

Coiled conductors 56 and 58 may each include a conductive core 64 and an insulation layer 66 surrounding wire 64. Wire 64 may include one or more conductive filars. In the example illustrated in FIG. 5, wire 64 is a solid core conductor. However, in other examples, wire may include a plurality of conductive filars that together form wire 64. Wire 64 or the conductive filars forming wire 64 may be made from any of a variety of conductive materials, such as tantalum, platinum, silver, or any other conductive material, or a combination of conductive materials, including alloys (such as nickel-cobalt-chromium-molybdenum alloy). Coiled conductors 56 and 58 may have the same wire 64 or different wires 64.

Insulation layer 66 surrounding wire 64 may be made from any of a number of non-conductive materials, such as soluble imide (SI), parylene, tantalum pentoxide, polyether ether ketone (PEEK), liquid crystal polymer (LCP), ethylene tetrafluroethylene (ETFE), polytetrafluroethylene (PTFE), perfluoroalkoxy (PFA), fluorinated ethylene propylene (FEP), urethanes, PurSil™, Tetrafluoroethylene/hexafluoropropylene/vinylidene fluoride (THV), or other non-conductive material or combination of non-conductive materials. A thickness of insulation layer 66 may be dependent on a number of factors, including the type of material used, a desired flexibility, a desired rigidity, a desired reliability, desired dielectric strength or other factor. When insulation layer 66 is made from SI, for example, insulation layer 66 may have a thickness of approximately 0.2-0.6 mils (0.0002-0.0006 inches). However, the thickness of insulation layer 66 may be larger or smaller.

Coiled conductors 56 and 58 are enclosed within lead outer jacket 52, which is exposed to the body of patient 12. Lead outer jacket 52 has a thickness (labeled "t" in FIG. 3B) that is thin enough such that lead 50 effectively functions as a shunt to redirect high frequency energy induced on conductors 56 and 58 along a substantial portion of the length of lead 50, but thick enough to protect conductors 56 and 58 from exposure to the outer jacket. As will be described in more detail below, lead 50 essentially functions as a theoretical capacitor that has a high impedance at low frequencies (e.g., at the frequencies of electrical stimulation therapy) and a low impedance at high frequencies (e.g., frequencies associated with MRI device 16). The thickness of lead outer jacket 52 will vary based on the type of material from which lead outer jacket 52 is formed, the material and thickness of the insulation layer 66 of coiled conductors 56 and 58, the material and gauge of wire 64, the length of the lead, pitch of coil turns, diameter of lead, or the like.

Lead outer jacket 52 is formed such that it extends at least partially between turns of coiled conductors 56 and 58. Such a configuration results in a variation in thickness of lead outer jacket 52 depending on the location along the lead. As illustrated in FIG. 3B, for example, the thickness of lead outer jacket 52 is larger at the portions of lead outer jacket 52 extending between the turns of coiled conductors 56 and 58 than at the portions directly over the coiled conductors 56 and 58.

In some instances, lead outer jacket 52 only extends partially between turns of coiled conductors 56 and 58. In this case, there is at least some space between the portions of lead outer jacket 52 extending between turns of coiled conductors 56 and 58 and the inner tubing 54 around which the coiled conductors 56 and 58 are wound. The space between the portions of lead outer jacket 52 extending between turns of coiled conductors 56 and 58 and the inner tubing 54 may be filled with air. However, in other instances, the space may be filled with another material having a high dielectric constant. When extending partially between turns of coiled conductors 56 and 58, lead outer jacket 52 contacts only a portion of the outer surface of conductors 56 and 58 (e.g., insulation layers 66). Lead outer jacket 52, for example, may be configured to contact a length of the outer surface of conductors 56 and 58 along the arc of conductors 56 and 58 having a central angle (labeled "θ" in FIG. 3B) between 20 degrees and 180 degrees. In some instances the central angle may be between 45 degrees and 180 degrees. In other examples, the central angle may be greater than 180 degrees, but not surrounding the entire outer surface of conductors 56 and 58. The length of the arc of conductors 56 and 58 that lead outer jacket 52 contacts may vary along the lead outer jacket as the formation of lead outer jacket 52, e.g., via reflow, may vary slightly from turn to turn.

In the examples described above, the surface area of conductors 56 and 58 is circular. However, conductors with different shapes may be utilized. For example, conductors 56 and 58 have a surface area having other geometries, such as a square geometry, rectangular geometry, or the like. Such conductors may provide more conductor surface area with a shorter distance between the conductor and the body of the patient, and thus an increased capacitance.

Lead outer jacket 52 may be formed of a non-conductive, biocompatible material, including but not limited to silicone, polymers, fluoropolymers, thermoplastic, or other non-conductive material or combinations thereof. In one example, lead outer jacket 52 may be formed of polyurethane, such as 55D polyurethane, in which case the thickness of lead outer jacket 52 (labeled "t" in FIG. 3B) may be between 2-5 mils and, more preferably, between 2-3 mils. However, the thickness of non-conductive, biocompatible material forming lead outer jacket 52 may be larger than 5 mils as long as the desired capacitance is achieved. Forming lead outer jacket 52 from other non-conductive, biocompatible materials may result in different desired thicknesses based on the dielectric constant of the material and the resistance of the material to wear from flexing, rubbing, and other forces. The thickness of the non-conductive lead outer jacket 52 is designed such that lead 50 essentially functions as a theoretical capacitor in which one of the capacitive plates of the theoretical capacitor are conductors 56 and 58 and the other one of the capacitive plates of the theoretical capacitor is the blood/fluid/tissue of patient 12. Insulation layer 66 and lead outer jacket 52 function as the dielectric material between the capacitive plates. The parameters of lead outer jacket 52 are thus designed to achieve a desired capacitance range, such as between 0.8 nanoFarads (nF) and 10 nF. For a lead outer jacket having a thickness of approximately 2 mils of polyurethane, lead 50 may have a capacitance of approximately 2.6 nF. The capacitance may be smaller or larger than this range so long as the energy dissipated along the length of lead 50 provides adequate reduction in the heat dissipated at the electrodes.

In other examples, lead outer jacket 52 may be formed of a conductive or semi-conductive, biocompatible material. In one example, lead outer jacket 52 may be formed of a conductive polymer, such as poly(3,4-ethylenedioxythiophene)

(PEDOT), polyphenylene sulfide (PPS), polythiophene (PT), polypyrrole (PPY), polycarbazoles, polyindoles, polyazepines, polyanilines (PANI), or other conductive polymer. One example commercially available conductive polymer is BT DOT from Biotectix of Ann Arbor, Mich. In one example, the conductivity of outer jacket 52 may be formed to be approximately equal to conductivity of the body. Forming lead outer jacket 52 from a conductive, biocompatible material (such as a conductive polymer) may result in a lead outer jacket that has similar capacitance as in the thin, non-conductive lead outer jacket example, but with an increased thickness (t) of lead outer jacket 52. An increased thicknesses of lead outer jacket 52 may increase the resistance of lead outer jacket 52 to wear from flexing, rubbing, and other forces. Lead 50 still functions as a theoretical capacitor in this example, but the capacitive plates of the theoretical capacitor are conductors 56 and 58 and the conductive lead outer jacket, respectively. In this example, insulation layer 66 of conductors 56 and 58 functions as the dielectric material of the theoretical capacitor.

A thickness of inner tubing 54 may be dependent upon the thickness of the outer jacket 52 and a desired handling, e.g., stiffness. For some cardiac applications, the lead may be designed to have a total thickness of inner tubing 54 and outer jacket 52 that provides desirable handling and shunting capabilities. For cardiac applications, for example, the combined thickness inner tubing 54 and outer jacket 52 may be less than 5 mils to provide a desirable handling. However, for applications in which physicians may desire a stiffer feel, lead 50 may have a thicker combined thickness of inner tubing 54 and outer jacket 52.

To form lead outer jacket 52 in such a manner, a substrate material used for lead outer jacket 52 may be applied over the coiled conductors 56 and 58 and reflowed using a combination of appropriate temperature, time, pressure, or other parameter to cause the substrate layer to extend between turns of coiled conductors 56 and 58 to obtain the desired contact with conductors 56 and 58. In other words, the substrate material is reflowed to only partially extend between turns of coiled conductors 56 and 58 such that there is a gap between the portions of lead outer jacket extending between turns of coiled conductors 56 and 58 and the inner tubing 54. The parameters used for reflowing the substrate material to form lead outer jacket 52, however, should not result in the lead outer jacket 52 contacting or bonding with inner tubing 54. Such a reflow process may be viewed as a partial reflow process since the reflowing of the substrate material of lead outer jacket 52 does not fully reflow to contact or bond with inner tubing 54 or other layers of material. Although lead outer jacket 52 is described herein as being formed using a reflow technique, the substrate layer of material used for lead outer jacket 52 may be applied over coiled conductors 56 and 58 using any technique that provides the desired coverage of conductors 56 and 58 described above.

Having a lead outer jacket 52 that at least partially extends between turns of conductors 56 and 58 provides lead 50 with some desirable mechanical characteristics, such as tensile strength and torsional stiffness. Because the lead outer jacket only partially extends between the turns of conductors 56 and 58, the space between the lead outer jacket 52 and inner tubing 54 permits the turns of coiled conductors 56 and 58 to move relative to one another during flexing of lead 50, particularly at the flexed portion of lead 50. In other words, the portion of coiled conductors 56 and 58 located at the concave side of the flexed portion of lead 50 may move closer to one another and, in some instances, even contact one another. The portion of coiled conductors 56 and 58 located at the convex side of the flexed portion of lead 50 may separate from one another, thus increasing the distance between the turns on the convex side of the flexed portion of lead 50. In this manner, the strain on conductors 56 and 58 is reduced at the flexed portions of coil, which in turn increases the flex life of lead 50.

Conductors with high inductance may be more resistant to induced current by high frequency, e.g., RF fields, of MRI device 16. For coiled or wound conductors, for example, several parameters are determinative of its inductance: the diameter of wire 64, the pitch (p) of the coil (the distance between turns of the coil), the cross-sectional area occupied by the coil, and the number of coiled conductors. As such, the parameters of coiled conductors 56 and 58 along the helical path from the proximal end of lead 50 to the distal end of lead 50 may be designed to increase the inductance of coiled conductors 56 and 58. For example, the helical path followed by conductors 56 and 58 may have a substantially constant pitch when the lead 50 is in a relaxed, straight configuration, the pitch being selected to achieve a desired inductance. Lead outer jacket 52 that partially extends between the turns of coils 56 and 58 may assist in maintaining adequate spacing between turns of coils 56 and 58 along a substantial portion of lead 50 in addition to providing the increased tensile strength and torsional stiffness.

Figure 4A:
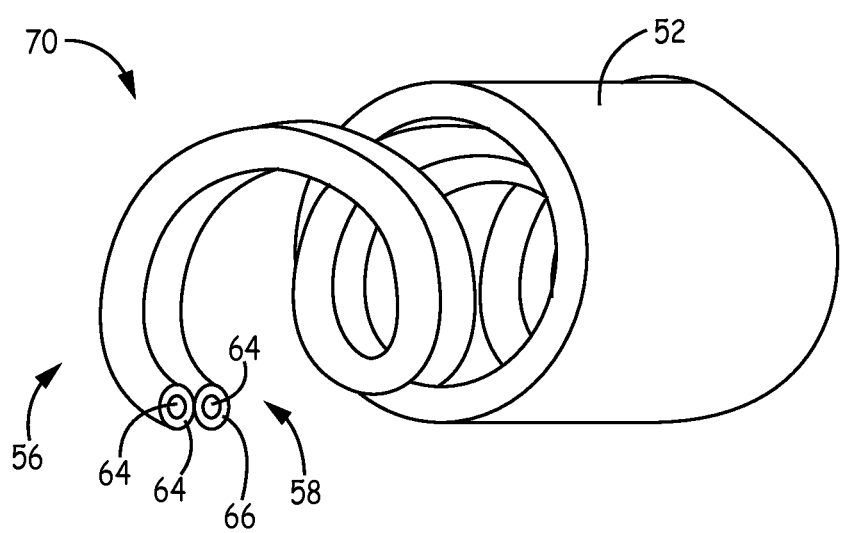
FIGS. 4A and 4B illustrate a partially cut away perspective view and a cross sectional view, respectively, along a length of a portion of another example lead.
Figure 4B:
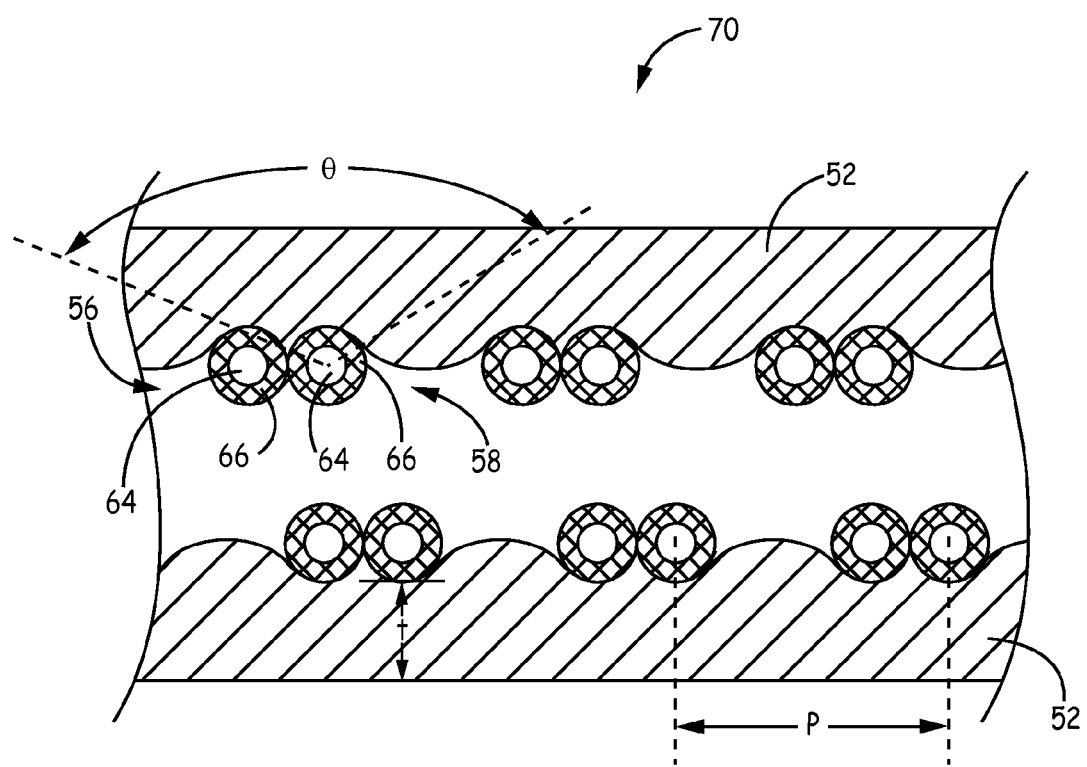

FIGS. 4A and 4B illustrate a portion of an example lead 70. Lead 70 is substantially similar to lead 50 of FIGS. 3A and 3B, but lead 70 does not include an inner tubing 70. Instead, lead outer jacket 72 has a thickness that provides the desired stiffness and mechanical stability. Lead outer jacket 72 may, for example, have a thickness that is at least 5 mils. Like the example above, lead outer jacket 52 may be made of a conductive, semi-conductive, or non-conductive material that is biocompatible. A conductive or semi-conductive material allows for a thicker lead outer jacket with increased capacitance.

Figure 5A:
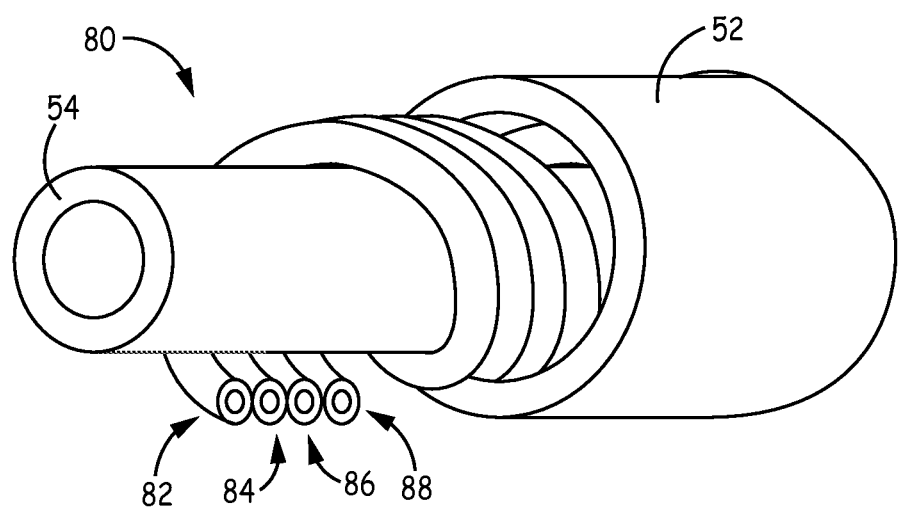
FIGS. 5A and 5B illustrate a partially cut away perspective view and a cross sectional view, respectively, along a length of a portion of another example lead.
Figure 5B:
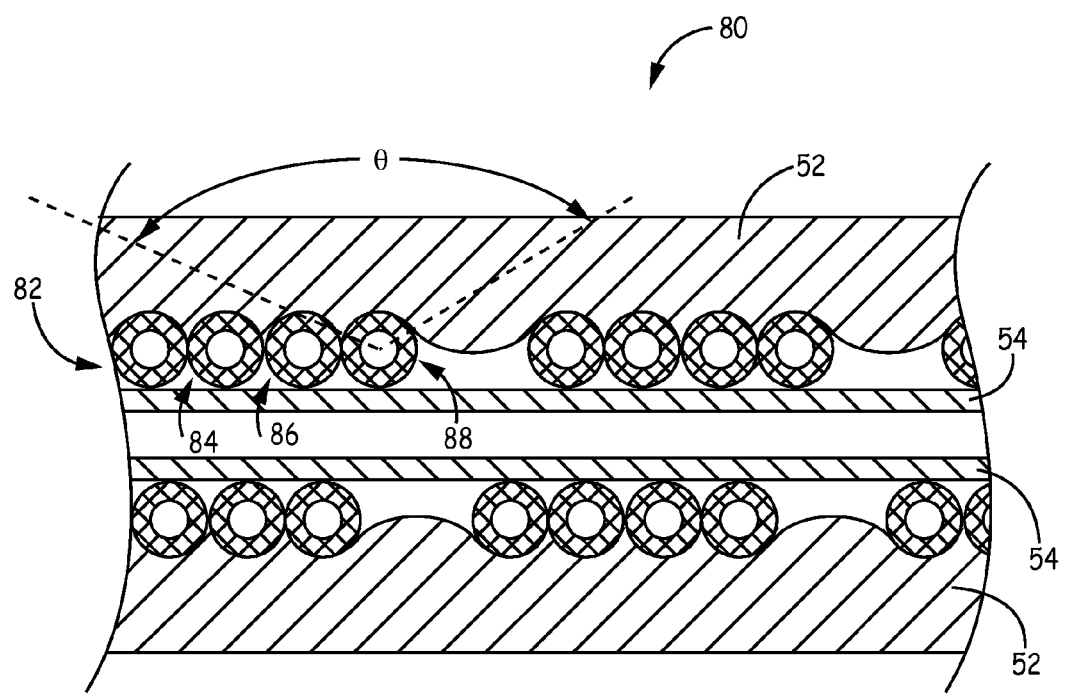

FIGS. 5A and 5B illustrate a portion of an example lead 80. Lead 80 is substantially similar to lead 50 of FIGS. 3A and 3B, but lead 80 includes four coiled conductors 82, 84, 86, and 88 instead of two coiled conductors 56 and 58. Each of coiled conductors 82, 84, 86, and 88 is electrically coupled to a respective electrode near the distal end of lead 80. As such, lead 80 is a multi-polar lead configuration. Although lead 80 is illustrated as including an inner tubing 54, in other embodiments, lead 80 may not include an inner tubing 54 (similar to lead 70 of FIGS. 4A and 4B).

Figure 6A:
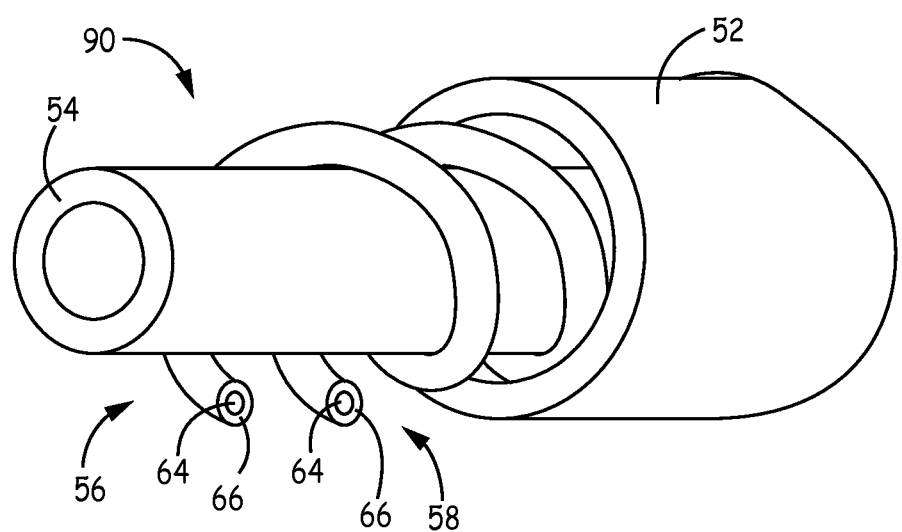
FIGS. 6A and 6B illustrate a partially cut away perspective view and a cross sectional view, respectively, along a length of a portion of another example lead.
Figure 6B:
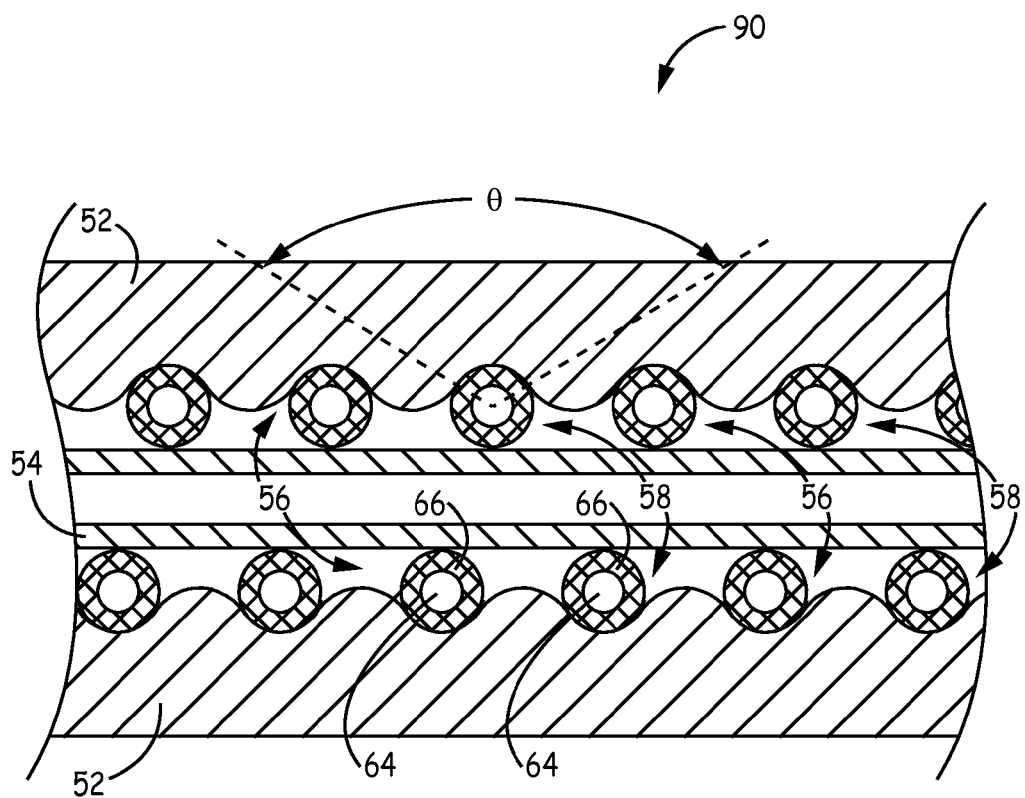

FIGS. 6A and 6B illustrate a portion of an example lead 90. Lead 90 is substantially similar to lead 50 of FIGS. 3A and 3B, but coiled conductors 56 and 58 are not wound side by side. Instead, coiled conductors 56 and 58 are spaced apart from one another.

Figure 7A:
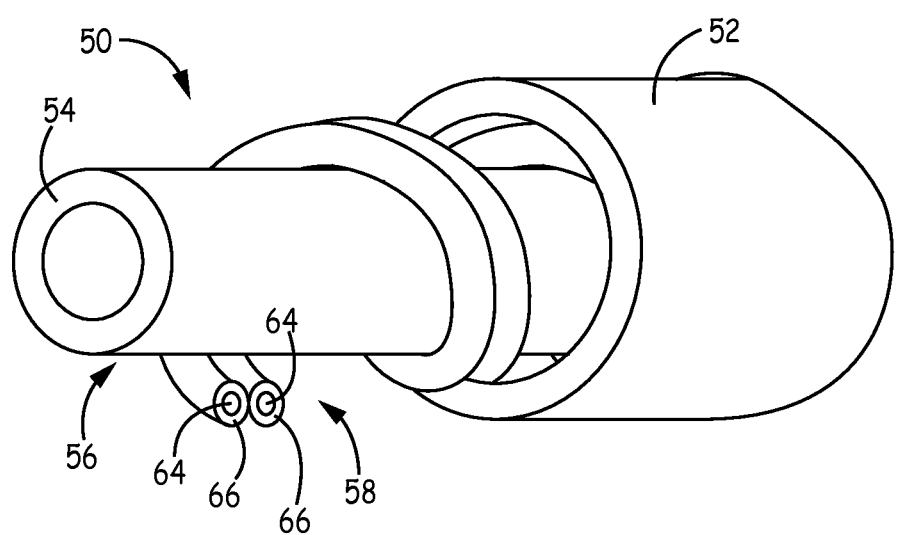
FIGS. 7A and 7B illustrate a partially cut away perspective view and a cross sectional view, respectively, along a length of a portion of another example lead.
Figure 7B:
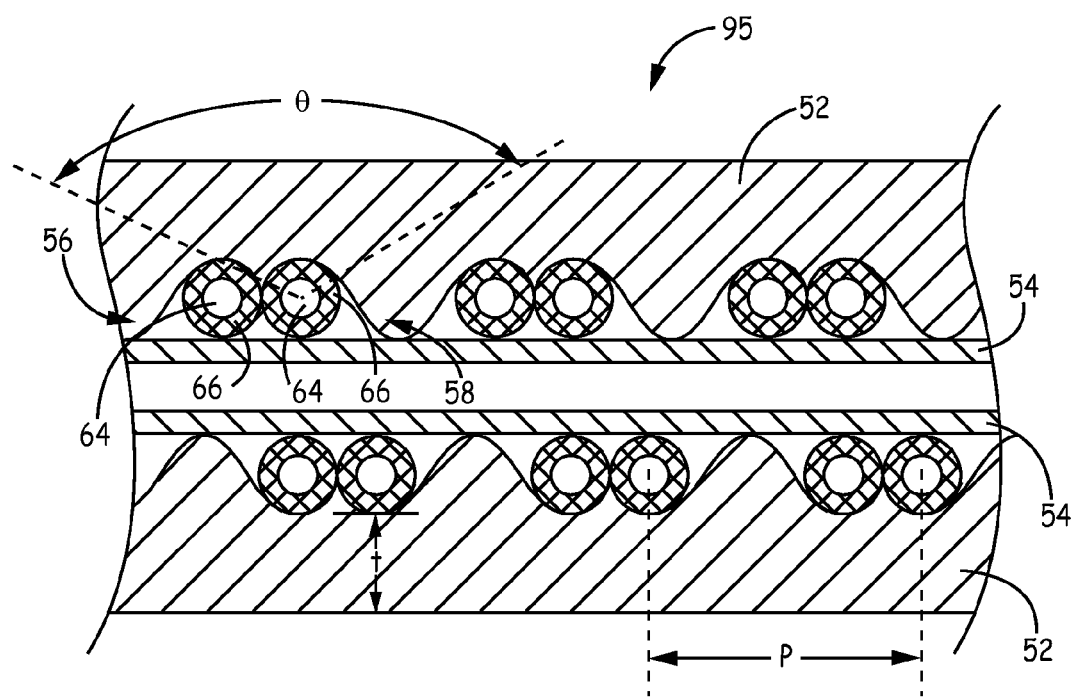

FIGS. 7A and 7B illustrate a portion of an example lead 95. Lead 95 is substantially similar to lead 50 of FIGS. 3A and 3B, but lead outer jacket 52 extends between turns of coiled conductors 56 and 58 and contacts inner tubing 54. However, outer jacket 52 and inner tubing 54 do not bond to one another.

In this example, lead outer jacket 52 still does not completely surround conductors 56 and 58. Instead, lead outer jacket 52 contacts a length of the outer surface of conductors 56 and 58 along the arc of conductors 56 and 58 having a central angle (labeled "θ" in FIG. 3B) that is less than or equal to 220 degrees, and more preferably 180 degrees. As such, the construction of lead outer jacket 52 leaves some air gaps adjacent to portions of conductors 56 and 58. Because lead outer jacket 52 does not bond to inner tubing 54 and there is some air gaps adjacent to conductors 56 and 58, conductors 56 and 58 may still move relative to one another during flexing of lead 95, particularly at the flexed portion of lead 95.

The various lead configurations illustrated in FIGS. 5 and 6 may also be formed such that lead outer jacket 52 extends to make contact with, but not bond to inner tubing 54.

Figure 8:
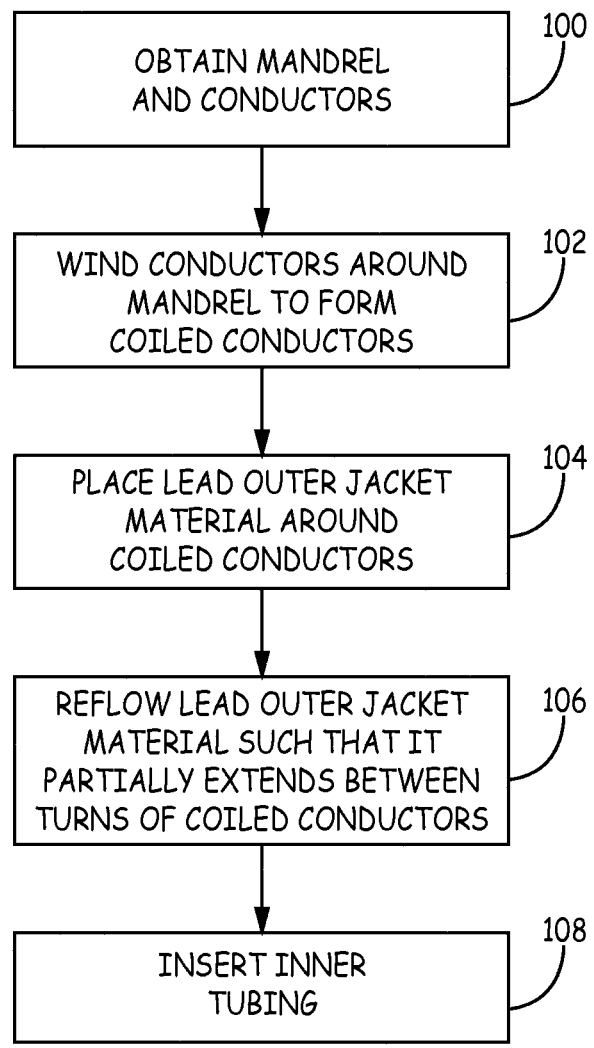
FIG. 8 is a flow diagram illustrating an example method of manufacturing a lead or a portion of a lead.

FIG. 8 is a flow diagram illustrating an example method of manufacturing a lead or a portion of a lead. Initially, a mandrel and one or more conductors (such as conductors 56 and 58) are obtained (100). The one or more conductors are wound around the mandrel to form a helical path that extends from one end of the mandrel to the other end of the mandrel (e.g., from the headstock to the tailstock) (102). The one or more conductors may be wound side by side as illustrated in FIGS. 3-5 and 7 or they may be spaced apart as illustrated in FIG. 6. The one or more conductors may be wound such that a pitch between the turns of the coiled conductors results in the coiled conductors having a high inductance.

After the one or more conductors are wound around the mandrel, a substrate material that will form lead outer jacket 52 is strung over the coiled conductors (104). The substrate material may be a non-conductive, semi-conductive, or conductive material that is biocompatible as described in detail above. The substrate material is reflowed such that the lead outer jacket extends partially between turns of the coiled conductors (106). The partial reflow may be achieved using a combination of appropriate temperature, time, pressure, or other parameter to cause the substrate layer to extend between turns of coiled conductors 56 and 58 to obtain the desired ingress of lead outer jacket 52 while leaving space for the coils to move upon flexing.

In some instances, an inner tubing (such as inner tubing 54) may be inserted within the lumen defined by coiled conductors 56 and 58 (108). In other instances, coiled conductors 56 and 58 may be wound around the inner tubing. In other words, the inner tubing may be placed over the mandrel prior to winding the inductors or the inner tubing may function as the mandrel. In embodiments in which the lead does not include an inner tubing, this step would not be performed. The majority of the outer jacket of the lead may be constructed in accordance with the method above. This portion of the lead outer jacket may then be connected to an electrode assembly at one end and a connector at the opposite end to form an entire lead.

Various embodiments of the disclosure have been described. It is understood that the present disclosure is not limited to leads for use in pacemakers, cardioverters or defibrillators. Other uses of the leads described herein may include uses in patient monitoring devices, or devices that integrate monitoring and stimulation features. Additionally, skilled artisans appreciate that other configurations and/or dimensions may be used for the mechanical and electrical elements described herein. It is also expected that the teachings herein, while described relative to a bipolar lead, can also be applied to a unipolar or multi-polar lead. These and other embodiments are within the scope of the following claims.

The invention claimed is:

1. An implantable medical lead having a proximal end configured to connect to an implantable medical device and a distal end, the lead comprising:
   a plurality of electrodes located near a distal end of the lead;
   a plurality of coiled conductors, wherein each of the plurality of coiled conductors extend along a length of the lead from the proximal end to a respective one of the plurality of electrodes located near the distal end; and
   an outer jacket configured to only partially extend between turns of at least one of the plurality of coiled conductors along the length of the lead from the proximal end to a respective one of the plurality of electrodes located near the distal end.

2. The implantable medical lead of claim 1, further comprising a non-conductive inner tubing around which the plurality of coiled conductors are wound, wherein the outer jacket is configured to partially extend between turns of the plurality of coiled conductors but not contact the inner tubing.

3. The implantable medical lead of claim 1, wherein the outer jacket is configured to contact a length of an outer surface of the conductors along an arc of the conductors having a central angle that is less than or equal to 180 degrees.

4. The implantable medical lead of claim 1, wherein the plurality of coiled conductors are co-radial such that each of the coiled conductors has substantially the same radius.

5. The implantable medical lead of claim 1, wherein the plurality of coiled conductors are co-axial such that at least some of the coiled conductors have a different radius from other ones of the coiled conductors, wherein the outer jacket is configured to only partially extend between turns of the coiled conductor having a largest radius.

6. The implantable medical lead of claim 1, wherein each of the plurality of coiled conductors includes a wire surrounded by an insulation layer.

7. The implantable medical lead of claim 1, wherein the outer jacket is formed from a non-conductive material.

8. The implantable medical lead of claim 7, wherein the non-conductive material of the lead outer jacket comprises one or more of a silicone, polymer, fluoropolymer, thermoplastic, or combinations thereof.

9. The implantable medical lead of claim 1, wherein the outer jacket is formed of a conductive or a semi-conductive material.

10. The implantable medical lead of claim 9, wherein the outer jacket is formed of a conductive polymer.

11. The implantable medical lead of claim 1, wherein the outer jacket has a thickness less than or equal to seven (7) mils.

12. The implantable medical lead of claim 11, wherein the outer jacket has a thickness less than or equal to three (3) mils.

13. The implantable medical lead of claim 1, wherein the lead comprises a multi-polar lead including four electrodes and four coiled conductors.

14. The implantable medical lead of claim 1, wherein the lead comprises a bipolar lead including two electrodes and two coiled conductors.

15. An implantable medical lead having a proximal end configured to connect to an implantable medical device and a distal end, the lead comprising:
   at least one electrode located near a distal end of the lead;
   at least one coiled conductor extending along a length of the lead from the proximal end to the electrode located near the distal end and electrically coupled to the electrode; and
   an outer jacket configured to only partially extend between turns of the coiled conductor along the length of the lead from the proximal end to the electrode located near the distal end.

16. The implantable medical lead of claim 15, further comprising a non-conductive inner tubing around which the at least one coiled conductor is wound, wherein the lead outer jacket is configured to partially extend between turns of the coiled conductor but not contact the inner tubing.

17. The implantable medical lead of claim 15, wherein the lead outer jacket is configured to contact a length of an outer surface of the at least one conductor along an arc of the at least one conductor having a central angle that is less than or equal to 180 degrees.

18. The implantable medical lead of claim 17, wherein the lead outer jacket is configured to contact a length of an outer surface of the at least one conductor along an arc of the at least one conductor having a central angle that is at least approximately 20 degrees.

19. The implantable medical lead of claim 15, wherein the at least one coiled conductor includes a wire surrounded by an insulation layer.

20. The implantable medical lead of claim 15, wherein the lead outer jacket is formed from a non-conductive material.

21. The implantable medical lead of claim 20, wherein the non-conductive material of the lead outer jacket comprises one or more of a silicone, polymer, fluoropolymer, thermoplastic, or combinations thereof.

22. The implantable medical lead of claim 15, wherein the lead outer jacket is formed of a conductive or a semi-conductive material.

23. The implantable medical lead of claim 22, wherein the lead outer jacket is formed of a conductive polymer.

24. The implantable medical lead of claim 15, wherein the lead outer jacket has a thickness less than or equal to five (5) mils.

25. A method comprising:
obtaining a mandrel having a first end and a second end;
winding one or more conductors around the mandrel from the first end of the mandrel to the second end of the mandrel;
placing a substrate material of a lead outer jacket over the wound conductors; and
reflowing the substrate material such that the lead outer jacket extends only partially between turns of the wound conductors from the first end of the mandrel to the second end of the mandrel.

26. The method of claim 25, wherein reflowing the substrate material comprises reflowing the substrate material such that the lead outer jacket contacts a length of an outer surface of the wound conductor along an arc of the conductor having a central angle that is less than or equal to 180 degrees.

* * * * *